United States Patent
Jinno et al.

(10) Patent No.: US 7,388,107 B2
(45) Date of Patent: Jun. 17, 2008

(54) PROCESS FOR PRODUCING (METH)ACRYLIC ACID OR (METH)ACROLEIN

(75) Inventors: Kimikatsu Jinno, Mie (JP); Yasushi Ogawa, Mie (JP); Yoshiro Suzuki, Mie (JP); Shuhei Yada, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/587,990

(22) PCT Filed: Oct. 20, 2004

(86) PCT No.: PCT/JP2004/015873

§ 371 (c)(1),
(2), (4) Date: Aug. 1, 2007

(87) PCT Pub. No.: WO2005/105714

PCT Pub. Date: Nov. 10, 2005

(65) Prior Publication Data

US 2007/0270610 A1  Nov. 22, 2007

(30) Foreign Application Priority Data

Apr. 30, 2004  (JP)  ............................ 2004-135311

(51) Int. Cl.
*C07C 51/16* (2006.01)
*C07C 45/00* (2006.01)

(52) U.S. Cl. ...................... 562/545; 568/479

(58) Field of Classification Search ............... None
See application file for complete search history.

(56) References Cited

U.S. PATENT DOCUMENTS 4,604,370 A * 8/1986 Sarumaru et al. ............ 502/38

6,437,193 B1 * 8/2002 Contractor et al. .......... 568/479

FOREIGN PATENT DOCUMENTS

| CN | 1263519 A   | 8/2000  |
|----|-------------|---------|
| JP | 61 033234   | 2/1986  |
| JP | 63 137755   | 6/1988  |
| JP | 03 170445   | 7/1991  |
| JP | 05 184945   | 7/1993  |
| JP | 11 263739   | 9/1999  |
| JP | 2000 256257 | 9/2000  |
| JP | 2000 513384 | 10/2000 |
| JP | 2002 53519  | 2/2002  |
| JP | 2003 306464 | 10/2003 |

OTHER PUBLICATIONS

U.S. Appl. No. 11/587,990, filed Oct. 30, 2006, Jinno et al.
U.S. Appl. No. 11/451,355, filed Jun. 13, 2006, Yada et al.
U.S. Appl. No. 11/547,864, filed Oct. 6, 2006, Ogawa et al.
U.S. Appl. No. 11/597,276, filed Nov. 20, 2006, Yada et al.
U.S. Appl. No. 11/596,287, filed Nov. 13, 2006, Jinno et al.

* cited by examiner

*Primary Examiner*—Paul A Zucker
(74) *Attorney, Agent, or Firm*—Oblon, Spivak, McClelland, Maier & Neustadt, P.C.

(57) ABSTRACT

A method for producing (meth)acrylic acid or (meth)acrolein, comprising a catalytic gas phase oxidation process for producing (meth)acrylic acid or (meth)acrolein by supplying propylene, propane, or isobutylene and a gas containing molecular oxygen to a reactor which contains a catalyst filled therein, wherein a gas containing molecular oxygen is supplied to the reactor having the catalyst filled therein during shutdown of the catalytic gas phase oxidation process does not lower the reaction activity of the catalyst and the selectivity of target products when re-starting the running after shutdown of the catalytic gas phase oxidation process.

18 Claims, No Drawings

PROCESS FOR PRODUCING (METH)ACRYLIC ACID OR (METH)ACROLEIN

CROSS REFERENCES TO RELATED APPLICATIONS

This application is a 371 of International Patent Application No. PCT/JP04/15873, filed on Oct. 20, 2004, and claims priority to Japanese Patent Application No. 2004-135311, filed on Apr. 30, 2004.

TECHNICAL FIELD

The present invention relates to a method for producing (meth)acrylic acid or (meth)acrolein at a good selectivity and a high yield by subjecting propylene, propane or isobutylene to catalytic gas phase oxydation with an oxygen-containing gas.

BACKGROUND ART

As a method for producing (meth)acrylic acid or (meth)acrolein, there is a method for subjecting propylene, propane, isobutylene to catalytic gas phase oxidation with an oxygen-containing gas in the presence of a catalyst to obtain (meth)acrolein, and further subjecting (meth)acrolein to catalytic gas phase oxidation to obtain a reaction gas including (meth)acrylic acid.

Here, (meth)acrolein means "acrolein or methacrolein", and (meth)acrylic acid means "acrylic acid or methacrylic acid".

In the above-described method, a catalyst for industrially producing (meth)acrylic acid or (meth)acrolein is a composite metal oxide, and a catalytic gas phase oxidation is continuously carried out while supplying a raw material and an oxygen-containing gas such as air in the presence of the catalyst at all times of normal running.

Where propylene, propane, isobutylene and (meth)acrolein, which are raw materials or intermediate products of (meth)acrylic acid or (meth)acrolein are blended with oxygen at a predetermined ratio, an explosive composition is formed which may result in an explosion by a firing source such as a high temperature substance or electric spark. Therefore, in order to protect production facilities from such an explosion and to automatically stop the production facilities safely, an automatic emergency stop apparatus (an interlock system) is installed, which discharges flammable gases in the apparatus out of the system by stopping supply of a flammable raw material and blowing inert gases such as a nitrogen gas, steam, etc., into the production facilities, when the explosive composition is formed.

When the running is re-started after such an emergent shutdown, or after a shutdown for a periodic inspection, there are cases where the reaction activity of a catalyst and selectivity of a target product are lowered.

In JP-A-2002-53519, a safe start-up method is disclosed in a catalytic gas phase oxidation reactor. However, no description is given of solving a problem due to which the reaction activity of a catalyst and selectivity of a target product after re-start of the running are lowered.

DISCLOSURE OF THE INVENTION

It is therefore an object of the invention to provide a method for producing (meth)acrylic acid or (meth)acrolein, comprising the steps of carrying out a catalytic gas phase oxidation by supplying propylene, propane, or isobutylene and a molecular oxygen-containing gas into a reactor in which a catalyst is filled, and obtaining a reaction gas containing (meth)acrylic acid or (meth)acrolein, wherein the reaction activity of the catalyst and selectivity of a target product are not lowered when re-starting the running after an emergent shutdown to secure safety or after shutdown for a periodic inspection.

Based on the result of studies carried out to achieve the above-described object, the inventors found that the reaction activity of a catalyst and selectivity of a target product are lowered where supply of a gas containing molecular oxygen (hereinafter merely referred to as "oxygen") into a reactor, in which the catalyst is filled, is stopped during a shutdown of a catalytic gas phase oxidation process, and only steam and gas not containing oxygen such as nitrogen are continuously supplied, and found that the catalyst performance is prevented from deteriorating by supplying a gas containing oxygen into a reactor during the shutdown. Thus, the invention was completed.

That is, the present invention provides a method for producing (meth)acrylic acid or (meth)acrolein of the following composition.

1. A method for producing (meth)acrylic acid or (meth)acrolein, comprising a catalytic gas phase oxidation process for producing (meth)acrolein or (meth)acrylic acid by supplying propylene, propane, or isobutylene and a gas containing molecular oxygen in a reactor having a catalyst filled therein, wherein a gas containing molecular oxygen is supplied in a reactor having the catalyst filled therein during shutdown of the catalytic gas phase oxidation process.

2. The method according to the above-described 1, wherein a gas containing molecular oxygen is supplied into a reactor by using a facility secured to be usable during shutdown of a catalytic gas phase oxidation process.

A catalyst used in a catalytic gas phase oxidation process in the producing method according to the invention is a composite metal oxide comprising a plurality of metals including Mo, etc., and since, even if molecular oxygen contained in the catalyst is used for an oxidation reaction of propylene, etc., during normal running, molecular oxygen in a gas reacting with propylene, etc. is supplied into the catalyst, an oxidation state of the catalyst is maintained. On the other hand, a reductive substance such as a partially heavy by-product is accumulated on the catalyst. Unless oxygen is continuously supplied with the temperature of the catalyst maintained in a state where the catalytic gas phase oxidation process stops, such a reductive substance uses oxygen of the catalyst and self-oxidizes to reduce the catalyst. Therefore, the oxidation state of the catalyst changes to cause the performance of the catalyst to deteriorate. It is presumed that, according to the method of the invention, since, even during a shutdown, molecular oxygen is supplied from outside to the catalyst in the reactor as during running, the oxidation state of the catalyst is maintained under a condition of a high temperature, and the performance of the catalyst does not deteriorate.

BEST MODE FOR CARRYING OUT THE INVENTION

Hereinafter, a detailed description is given of the invention.

With the producing method according to the invention, a mixed gas having propylene, isobutylene, etc. and an inert gas mixed and a gas containing molecular oxygen (hereinafter merely referred to as "oxygen") are supplied into a reactor having a catalyst filled therein, and (meth)acrylic acid or (meth)acrolein is produced by carrying out a catalytic gas phase oxidation process.

The following systems may be listed as the reaction method;

(Reaction Systems)

A one-path system, a non-reaction propylene recycling system, and a combustion waste gas recycling system described below are available as representative examples of the reaction system in an industrialized method for producing acrolein and acrylic acid. However, in the present invention, the reaction system includes these three systems and is not limited thereto.

(1) One-Path System:

The system is a method for mixing and supplying propylene, air and steam in the upstream reaction and converting the same mainly to acrolein and acrylic acid, and supplying the same to the downstream reaction without separating products from the outlet gas. At this time, a method for supplying air and steam necessary to be reacted in the downstream reaction to the downstream reaction in addition to the upstream outlet gas is common.

(2) Non-Reaction Propylene Recycling System:

In the system, a reaction produced gas containing acrylic acid, which is obtained in the downstream reaction, is introduced to an acrylic acid collecting apparatus, and acrylic acid is collected as an aqueous solution. A part of waste gas containing non-reacted propylene at the collecting apparatus side is supplied to the upstream reaction or the downstream reaction, wherein a part of the non-reacted propylene is recycled.

(3) Combustion Waste Gas Recycling System:

In the system, a reaction produced gas containing acrylic acid, which is obtained in the downstream reaction, is introduced to an acrylic acid collecting apparatus, and acrylic acid is collected as an aqueous solution. The total amount of waste gases at the collecting apparatus side is burned and oxidized, and non-reacted propylene, etc., contained therein are converted mainly to carbon dioxide and water, wherein a part of the combustion waste gases thus obtained is added to the upstream reaction or downstream reaction.

Generally, a tubular reactor is used when it is necessary to increase the productivity of a reactor with the performance of a catalyst highly maintained by strictly managing the reaction temperature of the catalyst and protecting the catalyst even where reaction heat is remarkably high as in an oxidation reaction.

In recent years, the production volume of acrylic acid from propylene and methacrylic acid from isobutylene (these acids are referred to as "(meth)acrylic acid" as a whole) has been remarkably increased in line with an increase in the demands thereof, wherein a number of plants have been constructed around the world, and the production scale per plant has been expanded to a hundred thousand tons or more annually. In accordance with enlargement of the production scale of plants, it becomes necessary to enlarge the production volume per oxidation reactor. As a result, load of a catalytic gas phase oxidation reactor of propane, propylene or isobutylene has been increased. In line therewith, a tubular reactor of higher performance has been demanded.

The invention employs a tubular reactor which includes, in the lengthwise direction of reactor tubes: a cylindrical reactor shell having a raw material supply port and a product discharge port; a plurality of annular conduits for introducing a heat medium into the cylindrical reactor shell or taking out the same therefrom, which are disposed on the outer circumference of the cylindrical reactor shell; a circulation apparatus for connecting the plurality of annular conduits to each other; a plurality of reaction tubes restricted by a plurality of tubular plates of the reactor and containing a catalyst; and a plurality of baffle plates for changing the direction of the heat medium introduced into the reactor shell, wherein a method for subjecting a substance to be oxidized, to catalytic gas phase oxidation with a gas containing molecular oxygen is preferably employed, and for example, at least any one of oxidation catalysts of Mo—Bi based catalyst and Mo—V based catalyst is filled up in the above-described reaction tubes.

The present invention pertains to a catalytic gas phase oxidation method for obtaining at least either one of (meth)acrolein and (meth)acrylic acid by catalytic gas phase oxidation with a gas containing molecular oxygen, using propylene, propane, isobutylene or (meth)acrolein or a mixture thereof as a substance to be oxidized. (meth)acrolein or (meth)acrylic acid or both thereof can be obtained from propylene, propane, or isobutylene. In addition, (meth)acrylic acid can be obtained from (meth)acrolein.

In the invention, a "process gas" means a gas pertaining to a catalytic gas phase oxidation reaction including a substance to be oxidized and a gas containing molecular oxygen as a raw material gas and a product obtained. Also, a "raw material" indicates a substance to be oxidized.

(Composition of Raw Material Gas)

A mixed gas of at least a substance to be oxidized of propylene, propane, isobutylene and (meth)acrolein, a gas containing molecular oxygen and an inert gas such as steam are mainly supplied, as a raw material gas, into a tubular reactor used for catalytic gas phase oxidation.

In the invention, the concentration of a substance to be oxidized in a raw material gas is 6 through 10% by mol, and oxygen is greater by 1.5 through 2.5 times by mol than the substance to be oxidized, and an inert gas is greater by 0.8 through 5 times by mol than the substance. The raw material gas introduced is divided into respective reaction tubes and passes through the respective tubes, and is reacted in the presence of an oxidation catalyst filled therein.

(Tubular Reactor)

The tubular reactor is widely used when producing (meth) acrylic acid or (meth)acrolein using a gas containing molecular oxygen in the presence of a composite oxide catalyst reacted by catalytic gas phase oxidation.

The tubular reactor used in the invention is generally used for industrial purposes. There is no special limitation. A tubular reactor which is preferably used is described in the specification of Japanese Patent Application No. 2003-416718.

A gas containing oxygen, which is used for the present invention, is, for example, air or a waste gas containing oxygen, which is generated in other production facilities, preferably air.

The above-described inert gas is steam, nitrogen or carbon dioxide gas which is industrially inexpensive. More inexpensively, a mixed gas which is collected and separated from a reaction gas obtained by catalytic gas phase oxidation may be recycled for use.

(Catalyst)

There are two types as a catalyst used for a catalytic gas phase oxidation reaction for producing (meth)acrylic acid or (meth)acrolein, one of which is used for the upstream reaction from olefin to unsaturated aldehyde or unsaturated acid, and the other of which is used for the downstream reaction from unsaturated aldehyde to unsaturated acid. In the invention, a catalyst which is adaptable to either of the reactions is favorable.

In the above-described catalytic gas phase oxidation reaction, a catalyst expressed by the following general formula (I) may be listed as an Mo-Bi based composite oxide catalyst used for the upstream reaction (reaction from olefin to unsaturated aldehyde or unsaturated acid) for producing mainly acrolein.

$$Mo_aW_bBi_cFe_dA_eB_fC_gD_hE_iO_x \qquad (I)$$

In the above-described formula (I), A denotes at least a type of element selected from nickel and cobalt, B denotes at least a type of element selected from sodium, potassium, rubidium, cesium, and thallium, C denotes at least a type of element selected from alkaline earth metals, D denotes at least a type of element selected from phosphor, tellurium, antimony, tin, cerium, lead, niobium, manganese, arsenic, boron, and zinc, E denotes at least a type of element selected from silicon, aluminum, titanium, and zirconium, and O expresses oxygen. Also, a, b, c, d, e, f, g, h, i and x respectively express an atomic ratio of Mo, W, Bi, Fe, A, B, C, D, E and O, wherein, when a=12, $0 \leq b \leq 10$, $0 < c \leq 10$ (preferably, $0.1 \leq c \leq 10$), $0 < d \leq 10$ (preferably, $0.1 \leq d \leq 10$), $2 \leq e \leq 15$, $0 < f \leq 10$ (preferably, $0.001 \leq f \leq 10$), $0 \leq g \leq 10$, $0 \leq h \leq 4$, and $0 \leq i \leq 30$, and x is a value determined by an oxidation state of respective elements.

A catalyst expressed by the following general formula (II) may be listed as an Mo—V based composite oxide catalyst which is used in the downstream reaction (reaction from the unsaturated aldehyde to unsaturated acid) for producing acrylic acid by oxidizing acrolein in the above-described catalytic gas phase oxidation reaction.

$$Mo_aV_bW_cCu_dX_eY_fO_g \qquad (II)$$

In the above-described general formula (II), X denotes at least a type of element selected from Mg, Ca, Sr and Ba, Y denotes at least a type of element selected from Ti, Zr, Ce, Cr, Mn, Fe, Co, Ni, Zn, Nb, Sn, Sb, Pb and Bi, and O denotes oxygen. a, b, c, d, e, f and g respectively indicate the atomic ratios of Mo, V, W, Cu, X, Y and O, wherein, when a=12, $2 \leq b \leq 14$, $0 \leq c \leq 12$, $0 < d \leq 6$, $0 \leq e \leq 3$, and $0 \leq f \leq 3$, and g is a numeral defined by the oxidation state of respective elements.

The above-described catalyst is produced by methods disclosed in, for example, JP-A-63-54942, JP-B-6-13096 and JP-B-6-38918.

The catalyst used for the invention may be a catalyst molded by an extrusion-molding method or a tablet compression-molding method or may be a catalyst in which a composite oxide composed of a catalyst component is carried on an inactive carrier such as silicon carbide, alumina, zirconium oxide, titanium oxide, etc.

Further, there is no special limitation in shapes of the catalyst used for the invention. The shape thereof may be any one of sphere, column, cylinder, star, ring, or irregularity.

(Diluent)

The above-described catalyst may be used with an inactive substance mixed therein as a diluent.

An inactive substance is stable under the above-described reaction conditions. It is not specially limited unless it has any specific reaction property with a raw material substance and a product. In detail, substances used as a carrier of the catalyst such as alumina, silicon carbide, silica, zirconium oxide, titanium oxide, etc., may be preferably employed.

Also, the shape thereof is not specially limited as in the catalyst. It may be either of spherical, columnar, cylindrical, star-like, ring-like, small piece-like, net-like, or irregular. The size thereof is determined in consideration of the diameter of reaction tubes and pressure losses.

The use amount of an inactive substance operating as the diluent may be adequately determined by a target catalyst activity.

(Adjustment of Catalyst Layer and Activity)

It is possible to vary the activity of the catalyst layer in reaction tubes.

As an adjustment method for adjusting to change the activities of the catalyst layers in the reaction tubes, a method for adjusting the activities of respective catalyst layers by using catalysts having different activities in respective catalyst layers by, for example, adjusting the composition of the catalysts or by diluting catalysts in which catalyst grains are mixed with inactive substance grains may be listed.

As a detailed example of the latter method, such a method may be listed, in which the catalyst layers are made into, for example, two layers, the catalyst layer at the inlet portion of a raw material gas of the reaction tubes is made into a catalyst layer having a higher ratio of inactive substance grains, that is, the use ratio of the inactive substance grains to the catalyst is made into, for example, 0.3 through 0.7 to bring about a low activity layer, and the catalyst layer at the outlet side of the reaction tubes is made into a high activity layer by setting the ratio to a low level, for example, 0.5 through 0.8 or by filling a catalyst which is not diluted.

The number of catalyst layers formed in the tubular axis direction of the tubular reactor is not specially limited. Since catalyst filling work becomes cumbersome and requires much labor if there are a number of the catalyst layers, it is recommended that the number of the catalyst layers is 1 through 10. In addition, the length of the respective catalyst layers is determined to an adequate value based on the type of catalyst, number of catalyst layers, and reaction conditions. Therefore, the length may be determined so that the effects of the invention are maximized.

As described above, it is possible to carry out catalytic gas phase oxidation according to the invention using a reactor having a catalyst and reaction tubes. The reaction gas obtained by the catalytic gas phase oxidation process includes objectives such as (meth)acrylic acid and (meth) acrolein, wherein the reaction gas is given to a separation process in order to obtain the objectives.

In normal running of the catalytic gas phase oxidation process, a gas containing oxygen for an oxidation reaction, for example, air is supplied into a reactor using a gas supplying device such as a compressor. On the other hand, since the gas supplying device is stopped during a shutdown for a periodic inspection or during a shutdown for an emergent situation, supply of propylene, propane, isobutylene, and a gas containing oxygen which are raw material gases into the reactor is stopped.

In the invention, the reactor is connected to a facility which can be used in an emergency so that, even during shutdown of the catalytic gas phase oxidation process, a gas containing oxygen such as air is supplied to a catalyst, wherein a gas containing oxygen is supplied to the reactor.

An apparatus for supplying air for metering facilities, a compressed gas holder, a gas supplying compressor connected to a failure-free power source may be listed as facilities which can be used during a shutdown.

It is preferable that the amount of supplying a gas containing oxygen to a reactor during a shutdown is 0.2 through 50 NL per hour per reactor tube. In a reactor having 10,000 through 30,000 reactor tubes, it is preferable that the amount of supplying a gas containing oxygen is 5 through 500 $Nm^3$ per hour per reactor, and 100 through 300 $Nm^3$ per hour per reactor is further preferable. Also, a gas containing oxygen, which is used at this time, may be a gas containing oxygen which is used for catalytic gas phase oxidization. However, air is preferably used.

Further, a gas containing oxygen is supplied until the running is re-started. In detail, the gas supply is continued until a gas containing oxygen is supplied to a reactor as a raw material gas.

Operation from normal running to stop and operation from a stop to re-start may be adequately carried out, depending on the production apparatus. For example, one example in a case where running is carried out to produce acrylic acid or acrolein from propylene is shown below.

[Predetermined Shutdown]
(During running, the temperature of the reactor is 300° C. or more and the pressure thereof is from atmospheric pressure to two times the atmospheric pressure or less)
(1) Stop of propylene
(2) Stop of steam and inert gas (The temperature is gradually lowered from 300° C. or more, and the pressure is normally from atmospheric pressure to two times the atmospheric pressure).
(3) The temperature is lowered with air supplied (The temperature is lowered to 130° C. or so. Since air temperature from an air compressor is high, the temperature cannot be lowered below 130° C., and the pressure is normally from atmospheric pressure to two times the atmospheric pressure or less).
(4) The air compressor is stopped, and the apparatus is made to open to cause the temperature to be further lowered (that is, from 130° C. to the room temperature, and the pressure is the atmospheric pressure). At this time, the apparatus at the downstream side of the apparatus (an apparatus in which the reaction outlet gas is processed) can be stopped.

A gas containing oxygen can be supplied to the reactor from the above-described stage (4), using, for example, an apparatus for supplying air for metering facilities (metering air).

[In the Case of an Emergent Shutdown]
(1) Propylene supply stops.
(2) An apparatus at the downstream of the reactor stops, and the reactor outlet gas is discharged into the atmosphere.
(3) Steam and inert gas are continuously supplied (The temperature is gradually lowered from 300° C. or more, and the pressure is normally from atmospheric pressure to two times the atmospheric pressure or less).
(4) The temperature naturally falls (The temperature is gradually lowered from 300° C. or more, and the pressure is normally from atmospheric pressure to two times the atmospheric pressure or less).
(5) If the states permit the running to be started, the following running start operation (2) is begun.
(6) If the operation of the air compressor is disabled, metering air is supplied (The temperature is gradually lowered from 300° C. or more, and the pressure is normally from atmospheric pressure to two times the atmospheric pressure or less).

A gas containing oxygen can be supplied to the reactor from the above-described stage (4), using, for example, an apparatus for supplying air for metering facilities (metering air). However, no gas is supplied in the case of the above-described (5).

[Operation from a Running-Shutdown State to Running Re-Start]
(1) Start-up of the apparatus at the downstream side of the reactor
(2) Starting of the air compressor
(3) Air is supplied from an air compressor to the reactor (The temperature rises from the room temperature to air temperature (120° C. or so), and the pressure is normally from atmospheric pressure to two times the atmospheric pressure or less).
(4) The temperature of the reactor is increased by a heating furnace or an electric heater (The temperature is increased from 120° C. or so to the running-start temperature of approx. 300° C., and the pressure is normally from atmospheric pressure to two times the atmospheric pressure or less).
(5) Running start conditions are determined (Raw materials (steam and inert gas) other than propylene are supplied under the running start conditions. The temperature is set to approx. 300° C., and the pressure is set to atmospheric pressure to two times the atmospheric pressure or less).
(6) Supply of propylene is started.

Supply of a gas containing oxygen into the reactor using metering air is stopped at the above-described stage (3).

EXAMPLE

Hereinafter, a detailed description is given of the invention on the basis of an example. However, the scope of the invention is not limited to the example.

Example 1

When executing an oxidation reaction of propylene, catalyst powder having a composition of Mo(12)Bi(5)Ni(3)Co(2)Fe(0.4)Na(0.2)B(0.4)K(0.1)Si(24)O(x) was produced as a catalyst. The numbers in the parentheses mean the atomic ratios. The composition (x) of oxygen is defined based on the oxidation state of respective metals. The catalyst powder was molded to form a solid catalyst, and the solid catalyst was used for reaction.

Using reaction tubes, made of stainless steel, whose length is 3.5 m, inner diameter is 24 mm $\phi$, outer diameter is 28 mm $\phi$, a fused salt of nitrate mixture, niter was used as a heating medium to maintain a reaction temperature.

1.5 liters of the above-described catalyst was filled in the reaction tube, and air of 50 NL per hour was supplied per reaction tube until the running started. The catalyst resided in the air atmosphere. With air supplied, the temperature of the reactor was increased from the room temperature to 320° C. Thereafter, while adjusting the reactor inlet pressure so that it becomes 75 kPa (Kilopascal) in terms of gage pressure, a raw material gas was supplied so that, under the condition of the heat medium temperature being 325° C., propylene becomes 150 NL per hour, steam becomes 150 NL per hour, air becomes 1125 NL per hour, and nitrogen becomes 75 NL per hour (Herein, NL means a cubic volume when the temperature is 0° C. and the pressure is atmospheric pressure).

The product gas was analyzed by gas chromatography, wherein the yields of products were as shown in Table 1.

TABLE 1

| Products | Yields |
| --- | --- |
| Acrolein + Acrylic acid | 91.5% |
| Carbon monoxide | 1.5% |
| Carbon dioxide | 2.6% |
| Acetic acid | 1.4% |
| Propylene | 3.0% |

Comparative Example 1

The running was carried out as shown below, using the catalyst and reaction apparatus, which were adjusted by the same method as that of Example 1.

Nitrogen was supplied in an amount of 50 NL per hour per reactor tube until the running starts after the catalyst was filled. It remained for one day as it was. The catalyst was in a nitrogen atmosphere. With nitrogen supplied, the temperature of the reactor was increased from the room temperature to 320° C. After that, while adjusting the reactor inlet pressure so that it becomes 75 kPa (Kilopascal) in terms of gauge pressure, a raw material gas was supplied so that, under the condition of the heat medium temperature being 325° C., propylene becomes 150 NL per hour, steam becomes 150 NL per hour, air becomes 1125 NL per hour, and nitrogen becomes 75 NL per hour. (Herein, NL means a cubic volume when the temperature is 0° C. and the pressure is atmospheric pressure).

The product gas was analyzed by gas chromatography, wherein the yields of products were as shown in Table 2.

TABLE 2

| Products | Yields |
| --- | --- |
| Acrolein + Acrylic acid | 89.3% |
| Carbon monoxide | 1.7% |
| Carbon dioxide | 4.2% |
| Acetic acid | 1.3% |
| Propylene | 3.5% |

On the basis of comparison of Table 1 to Table 2, it is found that the case of Example 1 in which a gas containing oxygen was supplied into a reactor, in which a catalyst is filled, before starting the running (that is, before supplying propylene) is superior in reaction activity of the catalyst and selectivity of target products.

While the invention has been described in detail and with reference to specific embodiments thereof, it will be apparent to one skilled in the art that various changes and modifications can be made therein without departing from the spirit and scope thereof.

This application is based on Japanese patent application (Patent Application No. 2004-135311) filed on Apr. 30, 2004, the entire contents thereof being hereby incorporated by reference.

INDUSTRIAL APPLICABILITY

According to the method of the invention, the reaction activity of a catalyst and selectivity of target products to produce (meth)acrolein or (meth)acrylic acid by subjecting propylene, propane or isobutylene to catalytic gas phase oxidation using a gas containing oxygen are maintained even in a case where running is re-started after the shutdowns.

The invention claimed is:

1. A method for producing (meth)acrylic acid or (meth)acrolein, comprising:
   (a) supplying propylene, propane, or isobutylene and a first gas comprising molecular oxygen to a reactor which contains a catalyst, to effect catalytic gas phase oxidation of said propylene, propane, or isobutylene, to obtain (meth)acrylic acid or (meth)acrolein; and
   (b) shutting down said reactor by reducing said supplying of said propylene, propane, or isobutylene;
   wherein a second gas comprising molecular oxygen is supplied to said reactor during said shutting down of said reactor, to maintain said catalyst in an oxidized state.

2. A method according to claim 1, wherein said second gas comprising molecular oxygen is supplied to said reactor by using a compressed gas holder or a compressor connected to a failure-free power source.

3. A method according to claim 1, wherein said reactor is a tube reactor.

4. A method according to claim 3, wherein said tube reactor comprises 10,000 to 30,000 reactor tubes.

5. A method according to claim 4, wherein said second gas comprising molecular oxygen is supplied to said reactor during said shutting down of said reactor in an amount of 0.2 to 50 NL per hour per reactor tube.

6. A method according to claim 1, wherein said second gas comprising molecular oxygen is air.

7. A method according to claim 1, wherein said catalytic gas phase oxidation of said propylene, propane, or isobutylene, to obtain (meth)acrylic acid or (meth)acrolein is carried out at a temperature of at least 300° C. and said shutting down of said reactor comprises cooling said temperature to about room temperature.

8. A method according to claim 7, wherein said reactor is a tube reactor.

9. A method according to claim 8, wherein said tube reactor comprises 10,000 to 30,000 reactor tubes.

10. A method according to claim 9, wherein said second gas comprising molecular oxygen is supplied to said reactor during said shutting down of said reactor in an amount of 0.2 to 50 NL per hour per reactor tube.

11. A method according to claim 7, wherein said second gas comprising molecular oxygen is air.

12. A method according to claim 1, further comprising: (c) restarting said reactor after said shutting down of said reactor.

13. A method according to claim 12, wherein said restarting of said reactor comprises re-supplying said propylene, propane, or isobutylene and said first gas comprising molecular oxygen to said reactor and raising the temperature of said reactor to at least 300° C.

14. A method according to claim 12, wherein said reactor is a tube reactor.

15. A method according to claim 14, wherein said tube reactor comprises 10,000 to 30,000 reactor tubes.

16. A method according to claim 15, wherein said second gas comprising molecular oxygen is supplied to said reactor during said shutting down of said reactor in an amount of 0.2 to 50 NL per hour per reactor tube.

17. A method according to claim 12, wherein said second gas comprising molecular oxygen is air.

18. A method according to claim 1, wherein said second gas comprising molecular oxygen is supplied to said reactor until said reactor is restarted.

* * * * *